US00PP37845P3

(12) United States Plant Patent
Tehrani et al.

(10) Patent No.: US PP37,845 P3
(45) Date of Patent: Nov. 17, 2026

(54) CHERRY TREE NAMED 'V69061'

(50) Latin Name: *Prunus avium*
Varietal Denomination: V69061

(71) Applicant: University of Guelph, Guelph (CA)

(72) Inventors: Ghassem Tehrani, Guelph (CA); James William Lay, Guelph (CA)

(73) Assignee: University of Guelph, Guelph (CA)

( * ) Notice: Subject to any disclaimer, the term of this patent is extended or adjusted under 35 U.S.C. 154(b) by 0 days.

(21) Appl. No.: 19/327,628

(22) Filed: Sep. 12, 2025

(65) Prior Publication Data

US 2026/0033412 P1 Jan. 29, 2026

Related U.S. Application Data

(63) Continuation-in-part of application No. 18/784,054, filed on Jul. 25, 2024.

(51) Int. Cl.

| | |
|---|---|
| ***A01H 5/08*** | (2018.01) |
| ***A01H 5/00*** | (2018.01) |
| ***A01H 6/74*** | (2018.01) |

(52) U.S. Cl.
USPC ..... Plt./181
CPC ..... *A01H 6/7445* (2018.05); *A01H 5/00* (2013.01); *A01H 5/08* (2013.01)

(58) Field of Classification Search
USPC ..... Plt./180, 181
See application file for complete search history.

(56) References Cited

U.S. PATENT DOCUMENTS

PP34,466 P2 * 8/2022 Subramanian ..... A01H 6/7445 Plt./184

* cited by examiner

*Primary Examiner* — Susan Mccormick Ewoldt
*Assistant Examiner* — Zachariah Allan Kay
(74) *Attorney, Agent, or Firm* — Weatherly IP Solutions, LLC; James M. Weatherly

(57) ABSTRACT

A new cherry tree particularly distinguished yellow fruit with a kidney shape, precocious fruiting habit, self-fertility, extremely tolerant to rain crack and moderate resistance to bacterial canker, is disclosed.

1 Drawing Sheet

Genus and species: *Prunus avium.*
Variety denomination: 'V69061'.

BACKGROUND OF THE NEW PLANT

The present invention comprises a new and distinct variety of cherry tree, botanically known as *Prunus avium* and hereinafter referred to by the variety name 'V69061'. 'V69061' originated from a controlled cross conducted in May 1969 between the female parent variety 'Van' (unpatented) and the male parent 'Stella' (unpatented). 'V69061' was bred and developed in Vineland, Ontario, Canada. The resulting seeds were germinated and one resulting seedling named 'V69061' was selected. Cherry cultivar 'V69061' was first asexually reproduced in Vineland, Onterio. Cherry cultivar 'V69061' was found to reproduce true to type in successive generations of asexual propagation via bud wood cuttings.

SUMMARY

The following are the most outstanding and distinguishing characteristics of this new variety when grown under normal horticultural practices in Wenatchee, Washington.

1. Yellow fruit with a kidney shape;
2. Precocious fruiting habit;
3. Self-fertile variety;

4. Extremely tolerance to rain crack; and
5. Moderate resistance to bacterial canker.

DESCRIPTION OF THE PHOTOGRAPH

This new cherry tree is illustrated by the accompanying photograph showing the fruit and leaves of 'V69061' from June 2019 on five year old plants grown in Wenatchee, Washington. The colors shown are as true as can be reasonably obtained by conventional photographic procedures.

DESCRIPTION OF THE NEW VARIETY

The following detailed descriptions set forth the distinctive characteristics of 'V69061'. The data which define these characteristics was collected in Wenatchee, Washington on five year old trees. All colour determinations were made using 2015 Royal Horticultural Society (R.H.S.) Colour Chart, $6^{th}$ edition.

Classification:
*Family.*—Rosaceae.
*Species.*—*Prunus avium* L.
*Denomination.*—'V69061'.

Parents:
*Female.*—'Van' (unpatented).
*Male.*—'Stella' (unpatented).

General:
*Height and spread.*—3.0 m×2.0 m.
*Cold hardiness.*—Zone 5.

*Diseases and pests.*—Extremely tolerance to rain crack; and Moderate resistance to bacterial canker (*Pseudomonas syringae*).
*Rootstock.*—Planted out on Gisela 6 (U.S. Plant Pat. No. 8,954).
*Propagation.*—Bud wood in August.
*Growth rate.*—1.0 m per season.
*Plant habit.*—Spreading.
*Branching density.*—Medium.
*Habit.*—Spreading.
*Fruiting habit.*—Precocious.

Trunk description:
*Size of trunk.*—7.5 cm at 30 cm height.
*Bark color.*—Young stems: Color: RHS 144B Strong Yellow Green. Older bark: Color: RHS N200A Dark Grayish Yellow Brown.
*Lenticels.*—RHS 156A.
*Description of dormant shoots* (*one year-old*).—Pubescence: Absent. Shoot size: Length: 1.0 cm. Width: 0.5 cm. Anthocyanin presence: Absent. Thickness of shoot at center of middle internode: 1.0 cm. Shoot angle: 45 Degrees. Branch internode length: 15 cm.
*Vegetative buds.*—Length: 1.0 cm. Width: 0.5 cm. Shape: Oval.
*Color of growing tip of shoot.*—RHS 144B Strong Yellow Green.
*Pubescence of shoots tip.*—Absent.
*Anthocyanin presence.*—Absent.

Foliage description:
*Leaf shape.*—Elliptical.
*Leaf division.*—Simple.
*Leaf base.*—Obtuse with two glands at the base.
*Leaf apex.*—Acute.
*Leaf fragrance.*—Absent.
*Leaf venation.*—Type: Dichotomous. Color: RHS 146A Upper Surface, RHS 146B Lower Surface.
*Leaf margins.*—Serrate.
*Leaf arrangement.*—Alternate.
*Leaf aspect.*—0.5°.
*Leaf attachment.*—Petiolate.
*Leaf surface* (*both surfaces*).—Smooth.
*Leaf size.*—Length: 13.5 cm. Width: 6.5 cm.
*Leaf color.*—Newly expanded leaves: Upper surface: RHS 146B. Lower surface: RHS 146A. Mature leaves: Upper surface: RHS 146A. Lower surface: RHS 146B.

Petioles:
*Length.*—3.5 cm.
*Width.*—0.2 cm.
*Color.*—RHS 146C.
*Anthocyanin.*—Absent.
*Texture.*—Smooth.

Inflorescence description:
*Blooming period.*—April 5 to 12 in Osoyoos, British Colombia Mid season.
*Lastingness of inflorescence.*—7 days.
*Flower fragrance.*—Cherry like fragrance.
*Flower quantity.*—Moderate, average of 75 flowers per branch.
*Flower type.*—Raceme.
*Flowers per raceme.*—Five.
*Flower size* (*diameter*).—1.5 cm.

Sepals:
*Number.*—Five.
*Shape.*—Conical.
*Base.*—Pointed.
*Apex.*—Pointed.
*Margin.*—Entire.
*Color.*—Upper surface: RHS 139C. Lower surface: RHS 138C.
*Texture.*—Upper surface: Smooth. Lower surfaces: Smooth.
*Length.*—0.6 cm.
*Calyx width.*—0.5 cm.

Petals:
*Number.*—Five.
*Arrangement.*—Intermediate.
*Shape.*—Obovate.
*Base.*—Obtuse.
*Apex.*—Acute.
*Margin.*—Entire.
*Length.*—1.7 cm.
*Width.*—0.6 cm.
*Color.*—RHS N155B.

Pedicels:
*Length.*—3.0 cm.
*Width.*—0.2 cm.
*Color.*—RHS 143B.
*Texture.*—Smooth.

Reproductive organs:
*Gynoecium.*—Pistil: Number: One. Length: 0.6 cm. Style: Color: RHS 143C. Length: 0.6 cm. Width: 0.1 cm. Stigma: Diameter: 0.1 cm. Color: RHS 142A. Ovary: Color: RHS 143C.
*Androecium.*—Filaments. Color: RHS 155D. Length: 1.0 cm. Anthers: Color: RHS 15C. Pollen: Amount: Large amount. Color: RHS 15C.

Fertility: Self Fertile.

Fruit description:
*Fruit type.*—Drupe.
*Fruit shape.*—Kidney.
*Fruit apex.*—Round.
*Fruit base.*—Chordate.
*Fruit firmness.*—Firm, 417 g/mm.
*Fruit set.*—Good.
*Fruit stalk.*—Length: 4.0 cm. Thickness: 0.2 cm. Surface: Smooth. Color: RHS 143B.
*Fruit bearing.*—Yes.
*Number of fruit per cluster.*—Three.
*Lenticels.*—Very small to absent.
*Overall skin color.*—RHS N45A.
*Skin ground color.*—RHS 13B (yellow-orange).
*Skin overcolor.*—RHS 44A (Medium red), medium (50-60%), mottled and blushed pattern.
*Harvest date.*—June 14 in Osoyoos, British Colombia, 10 days before Rainier.
*Skin thickness.*—Medium.
*Skin surface.*—Smooth.
*Flesh color.*—RHS 11A, yellow.
*Juice.*—Description: Color: Clear.
*Apex end.*—Color: RHS N45A.
*Fruit use.*—Fresh market.
*Weight.*—12 grams.
*Acidity.*—0.68 g/100 g.
*Storage life.*—6 weeks.
*Productivity.*—20,000 lbs. per acre.

Seeds:

*Number per berry.*—One.

*Color.*—RHS 23A.

*Size.*—Length: 1.0 cm. Width: 0.8 cm.

*Shape.*—Elliptical.

COMPARISON WITH PARENTAL LINES AND KNOWN VARIETY

'V69061' is distinguished from its parents as described in Table 1.

TABLE 1

| Comparison with Parents | | | |
|---|---|---|---|
| Characteristic | 'V69061' | Female parent | Male parent |
| Self-Fertility | Yes | No | Yes |
| Rain Crack Resistant | Yes | No | No |

'V69061' is most similar to the commercial cherry named 'Rainier' (unpatented). Differences between the two varieties are described in Table 2:

TABLE 2

| Characteristics | 'V69061' | 'Rainier' |
|---|---|---|
| Self-Fertility | Yes | No |
| Bacterial Canker Resistance | Yes | No |

Table 3 below provides a comparison of 'V69061' with four cherry varieties, 'V690630' (U.S. Plant patent application Ser. No. 19/327,484), 'V69068' U.S. Plant patent application Ser. No. 19/327,359), 'V69062' (U.S. Plant patent application Ser. No. 19/327,254), 'V690628' (U.S. Plant patent application Ser. No. 19/327,761), with pending U.S. patent applications:

TABLE 3

| Cultivar | 'V690630' | 'V69061' | 'V69062' |
|---|---|---|---|
| Ripening Time | 10 days before the 'Bing' variety | 10 days before the variety 'Rainier' | Same as variety 'Bing' |
| Fruit Size mm | 29 | 29 | 30 |
| Firmness g/mm | 711 | 417 | 520 |
| Brix | 18 | 17 | 18 |
| Acidity g/100 g | 0.80 | 0.68 | 0.78 |
| Fruit Shape | Kidney to flat-round | Kidney | Flat-round |
| Growth Habit | Spreading | Spreading | Spreading |
| Fruiting Habit | Precocious | Precocious | Very Precocious |
| Stem Length | Short | Medium-Long | Medium |
| Flesh colour | Black-red | Yellow | Dark red |
| Disease | Moderately resistant to bacterial canker | Moderately resistant to bacterial canker | Moderately resistant to bacterial canker |
| Rain-induced cracking | Less susceptible | Extremely Tolerant | Very Tolerant |

TABLE 3-continued

| Cultivar | 'V690628' | 'V69068' |
|---|---|---|
| Ripening Time | Three days before variety 'Bing' | Three days after Bing varieties |
| Fruit Size mm | 30 | 27 |
| Firmness g/mm | 413 | 435 |
| Brix | 18 | 18 |
| Acidity g/100 g | 0.55 | 0.78 |
| Fruit Shape | Kidney to flat-round | Flat-round |
| Growth Habit | Spreading | Spreading |
| Fruiting Habit | Precocious | Highly Precocious |
| Stem Length | Medium | Long |
| Flesh colour | Dark red-purple | Red |
| Disease | Moderately resistant to bacterial canker | Moderately resistant to bacterial canker |
| Rain-induced cracking | Good resistance | Less susceptible |

We claim:

1. A new and distinct cultivar of cherry tree named 'V69061' as illustrated and described herein.

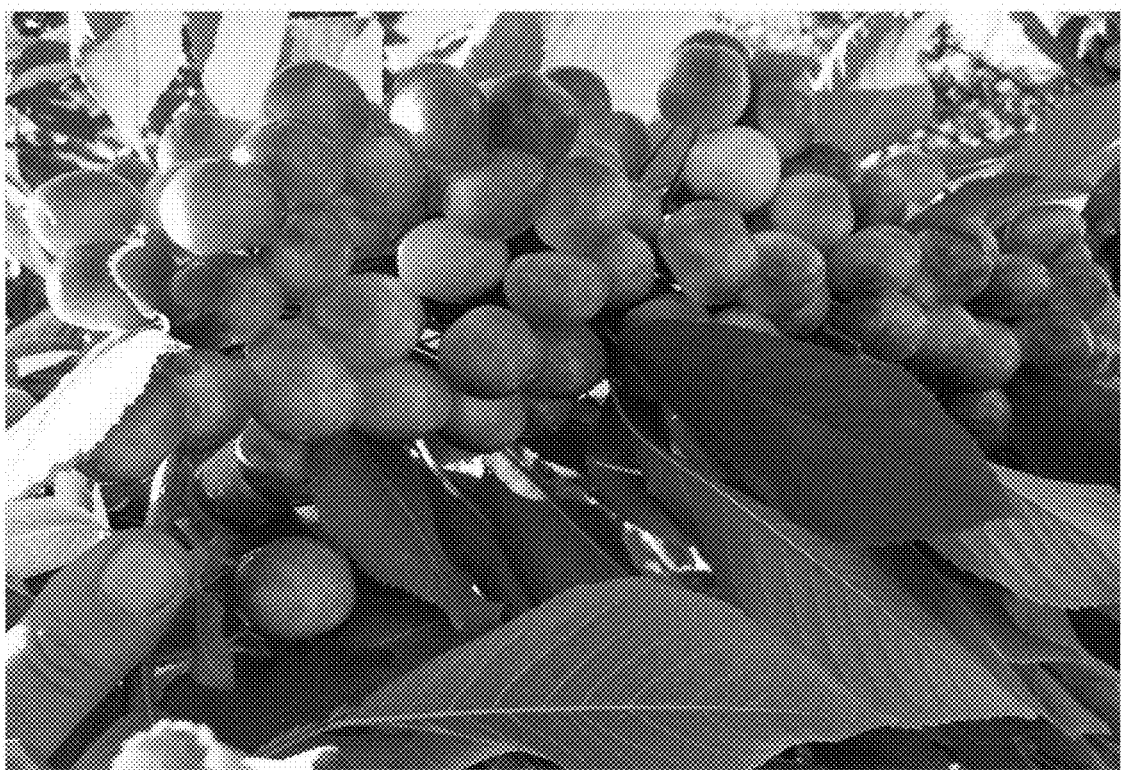

* * * * *